United States Patent [19]

Scott

[11] Patent Number: 5,002,046

[45] Date of Patent: Mar. 26, 1991

[54] BALANCED SKELETAL TRACTION APPARATUS

[76] Inventor: James W. Scott, 403 W. 16th St., Tifton, Ga. 31794

[21] Appl. No.: 410,826

[22] Filed: Sep. 22, 1989

[51] Int. Cl.⁵ .............................................. A61F 5/04
[52] U.S. Cl. ................................... 128/83; 128/84 R; 128/84 C
[58] Field of Search ..................... 128/83, 84 R, 84 B, 128/84 C, 882, 85

[56] References Cited

U.S. PATENT DOCUMENTS

| | | | |
|---|---|---|---|
| 432,888 | 7/1890 | Miller | 128/85 |
| 885,243 | 4/1908 | Haas | 128/75 |
| 1,231,839 | 7/1977 | Berlin | 128/68 X |
| 1,577,782 | 3/1926 | Atkinson | 128/85 |
| 1,890,372 | 12/1932 | Ettinger | 128/85 |
| 1,904,942 | 4/1933 | Heigl | 128/84 |
| 2,521,530 | 9/1950 | McGuffage | 128/69 X |
| 2,631,582 | 3/1953 | Bensfield | 128/84 C |
| 2,768,622 | 10/1956 | Sanders | 128/71 |
| 3,149,630 | 9/1964 | Schmidt | 128/84 R |
| 3,333,286 | 8/1967 | Biolik | 5/431 |
| 3,378,861 | 4/1968 | Lousberg | 5/432 |
| 3,461,864 | 11/1969 | Coss | 128/85 |
| 3,765,411 | 10/1973 | Ward, Jr. | 128/84 C |
| 3,775,785 | 12/1973 | Mittendorf | 5/442 |
| 3,800,787 | 4/1974 | Rush | 128/84 R |
| 3,853,121 | 12/1974 | Mizrachy et al. | 128/DIG. 20 |
| 3,995,846 | 12/1976 | Frick | 128/83 X |
| 4,336,796 | 6/1982 | Andrews et al. | 128/87 R |
| 4,367,870 | 1/1983 | Birch | 128/70 X |
| 4,502,170 | 3/1985 | Morrow | 128/80 R X |
| 4,602,619 | 7/1986 | Wolf et al. | 128/75 |
| 4,664,099 | 5/1987 | Pearl, Jr. | 128/84 C X |

FOREIGN PATENT DOCUMENTS

| | | | |
|---|---|---|---|
| 2038487 | 2/1972 | Fed. Rep. of Germany | 128/84 C |
| 3713360 | 11/1988 | Fed. Rep. of Germany | 128/83 |
| 897239 | 1/1982 | U.S.S.R. | 128/87 R |
| 1074523 | 2/1984 | U.S.S.R. | 128/87 R |

OTHER PUBLICATIONS

J. B. J. S., vol. XVIII, No. 1, 1/1936, pp. 234–235 by A. Marians, M.D.
Siebrandt Mfg. advertisement, 4/1932.
Hawley Scanlon System brochure, 5/1936.
Medical-Surgical Review, Widolf Leg Splint, 1971.

Primary Examiner—Robert A. Hafer
Assistant Examiner—Kevin G. Rooney
Attorney, Agent, or Firm—Bradford E. Kile

[57] ABSTRACT

A balanced skeletal traction apparatus for aligning fractured leg bones of a patient lying in a supine recuperative position including an underlying solid polygon support member, a horizontal traction device operable to be connected to a patient's lower leg for providing longitudinal traction and at least one securing member operable to releasably secure a patient's leg with respect to the underlying solid polygon support member.

19 Claims, 2 Drawing Sheets

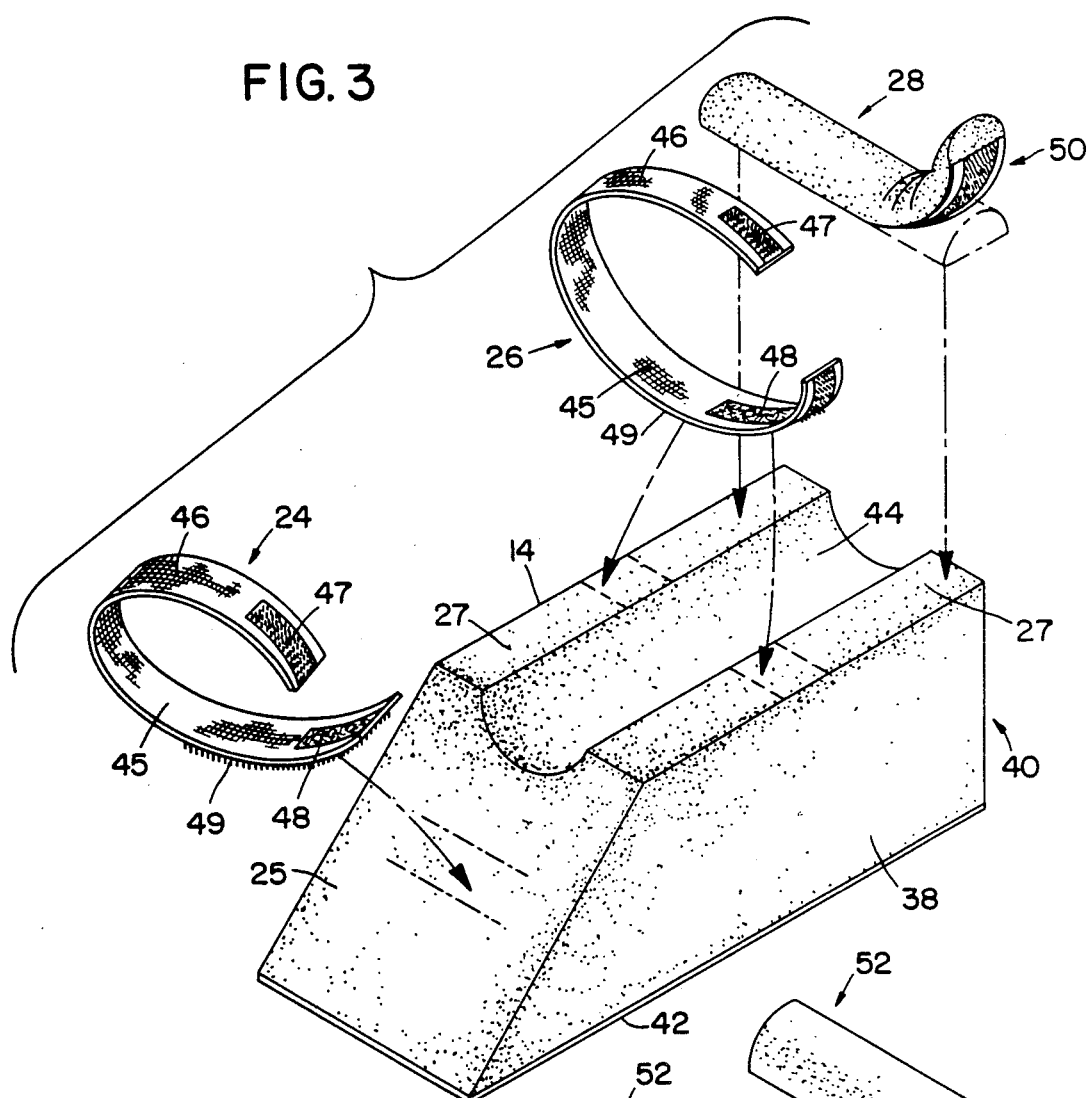

BALANCED SKELETAL TRACTION APPARATUS

BACKGROUND OF THE INVENTION

This invention relates to a novel balanced skeletal traction apparatus. More specifically, this invention relates to a balanced skeletal traction apparatus used for aligning fractured leg bones of a patient following surgery or injury.

When a portion of a bone is fractured, it is necessary to position the fractured fragments so that the fragments will successfully align and rejoin to insure resumption of a structural bone member. Reduction, as applied to fractures, refers to the means employed to bring the fracture fragments back into close apposition and alignment. Immobilization, as applied to fractures, refers to the means employed to maintain the reduction until successful repair of the fracture has occurred. In this connection, three principal factors determine, to a large extent, whether the fractured fragments will heal successfully. First, the accuracy of the reduction of the displaced fracture fragments is essential. Second, efficiency of the immobilization by which the fracture fragments are held in the reduced position is important. Third, the local blood supply available to the fracture fragments must be maintained to facilitate proper bone knitting between adjacent fragments.

Insufficient reduction may result in malunion, delayed union, or nonunion of the fracture. All of these maladies complicate and extend the recuperative process. It is therefore highly desirable to promote and facilitate the reduction of and blood supply to the fractured fragments of a leg bone so that the fractured fragments may heal. A successful method of treatment is based first on obtaining reduction and then maintaining reduction until fracture healing occurs in a bone while concurrently encouraging an adequate blood supply to the injured area. A common means of both obtaining and maintaining reduction is through the use of traction devices.

Traction has been used to treat fractures for hundreds of years and is still the most commonly indicated method of treatment. Traction is classified as being applied through either skin or bone, and may be further classified by the direction of the traction (i.e. horizontal, vertical, or oblique). In practice, traction is exerted on the distal fracture fragment, aligning it with the less manageable proximal fragment.

Horizontal skin traction was first applied in the 14th century for the treatment of femoral fractures. A method commonly used in the past was introduced during the American Civil War. Named Buck's traction after its inventor, this type of simple traction aligns femoral fracture fragments in a horizontal direction. A patient lying in a supine position has strips of ordinary adhesive tape applied to the sides of the leg and attached to a spreader block at the foot. The leg is wrapped with an elastic bandage to improve purchase of the tape on the skin. A piece of traction cord attaches the spreader block to a weight, which is hung over the foot of a bed. The lower leg is supported on a pillow to reduce friction of the heel against the bed linen. Countertraction is supplied by elevating the foot of the bed on shock blocks. A disadvantage of this type of traction is that supporting the lower leg on a pillow invites unintentional patient rotation of the lower leg and corresponding complications connected with disturbance of the fracture fragments during the healing process.

Vertical skin traction has been popular since being introduced in the 1870s. Its popularity is based on the effectiveness of maintaining fracture alignment and the fact that it especially facilitates care of an infant or child in bed. An early vertical skin traction configuration included tape which secured a spreader block to the lower leg, as described above. The leg was vertically attached to a suspension means, thereby aligning the fracture fragments.

Many disadvantages were associated with this configuration. Reduction of blood flow and associated circulation impairment tended to occur in the normal as well as the fractured limb. If a patient moved toward the foot of the bed, hyperextension of the knee further jeopardized limb circulation. Moreover, the circumferential wraps required to hold the traction tapes in place added to the problem of circulation impairment. This device for vertical traction was improved by lowering the inclination of the leg to about 45 degrees, versus 90 degrees, thus reducing the risk of vascular compromise. However, problems of the type previously described still remained.

Oblique skin traction has been commonly used in several forms, employing various means of supporting the leg, and producing a resultant traction. In the past the weight of the fracture fragments was supported by a sling to prevent posterior angulation. Russell's method for oblique skin traction was introduced in 1921 and is often employed by attending physicians. This method is used for children and adults and provides a single traction system for both vertical and horizontal traction by means of a sling beneath the proximal leg or knee and longitudinal traction along the distal portion of the leg, respectively. A traction doubling pulley system was particularly applicable to adults who required substantial longitudinal traction to prevent shortening of the healing bone.

Russell's method of skin traction limited versatility by attaching both the vertical and horizontal traction means to a single pulley. An improvement over this configuration was realized when the vertical support sling and the distal traction elements were separated with independent pulleys and weights. This system provided greater flexibility.

In this improved traction device, the force counteracting the fracture fragments is the resultant force of the vertical sling and the horizontal traction along the leg. For this reason it is important that the vertical sling be under the proximal leg rather than under the thigh. If the sling is placed under the thigh, the force is directed more cephalad with less resultant force. This cephalad force can also cause anterior angulation to occur at the fracture site. The vertical sling must be at least 90 degrees or slightly caudal to the horizontal pull along the leg to achieve an adequate resultant force. A second force, the pull of gravity, can produce posterior bowing at the fracture site. In order to counter this force, a pillow was placed under the thigh to prevent the posterior bowing.

Problems associated with the previously described system include difficulties involved in assembling such a complex system of pulleys. Multiple medical personnel are needed to accurately align and reduce the fractured fragments. It is also difficult to make adjustments to the direction of traction or the traction force because of the interaction between the pulleys. Further, a patient's movement is almost completely restricted and therefore tends to make recuperation an uncomfortable process.

The difficulties suggested in the preceeding are not intended to be exhaustive but rather are among many which may tend to reduce the effectiveness and physician satisfaction with prior balanced skin traction devices. Other noteworthy problems may also exist; however, those presented above should be sufficient to demonstrate that balanced skeletal traction devices appearing in the past will admit to worthwhile improvement.

OBJECTS AND BRIEF SUMMARY OF THE INVENTION

Objects

It is therefore a general object of the invention to provide a novel balanced skeletal traction device which will obviate or minimize difficulties of the type previously described.

It is a specific object of the invention to provide a balanced skeletal traction device which may be used to bring fracture fragments of a leg bone into close apposition to each other so that normal position, length, and alignment of the bone can be restored.

It is another object of the invention to provide a balanced skeletal traction device which allows facile alignment of a patient's fracture fragments.

It is still another object of the invention to provide a balanced skeletal traction device which minimizes the number of medical personnel necessary to prepare and position a patient in a traction device.

It is a further object of the invention to provide a balanced skeletal traction device which allows for facile adjustment of a traction force provided to a patient.

It is yet a further object of the invention to provide a balanced skeletal traction device which securely maintains the fracture fragments so that healing may proceed.

It is still a further object of the invention to provide a balanced skeletal traction device which encourages sufficient blood flow to the fractured fragments and the extremities of a patient's leg bone.

It is yet another object of the invention to provide a balanced skeletal traction device which maintains the reduced fracture fragments of a patient in a comfortable manner while the patient is reclined in a recuperative supine position.

It is yet still another object of the invention to provide a balanced skeletal traction device which is easily manufactured, easily personalized to various sized patients, and inexpensive and thus disposable.

Brief Summary of a Preferred Embodiment of the Invention

A preferred embodiment of the invention which is intended to accomplish at least some of the foregoing objects includes an underlying support member comprising a solid polygon. The solid polygon has an inclined surface for supporting a back portion of a patient's thigh and a generally horizontal upper surface, continuous with the inclined surface, for supporting a patient's lower leg. The horizontal surface of the solid polygon includes an arcuate elongated groove which cradles, restrains, and receives a patient's lower leg. The solid polygon further includes two generally vertical lateral surfaces, a generally vertical distal end surface and a substantially flat bottom surface. The flat bottom surface has a low coefficient of friction relative to the other surfaces of the polygon.

A horizontal traction assembly is attached to a patient's lower leg and provides longitudinal traction to the fracture fragments of a patient's leg. A lower leg sleeve member envelops a patient's lower leg and is secured to a U-shaped support member. The U-shaped support member includes a pair of support arms which extend along opposing lateral portions of a patient's lower leg and add a desirable degree of rigidness to the sleeve member. At the byte portion of the U-shaped support member a transverse bar extends between opposing arms and is connected to a tension system. The tension system comprises a pulley and an associated stack of weights which controls the magnitude of the traction force delivered to the patient's recuperating bone.

Elastic securing straps, operable to circumferentially attach around the lower and/or upper portions of a patient's leg, secure the leg to the solid polygon. The securing straps secure a patient's leg in a stable position and allow facile adjustment as necessitated by the patient.

In a further embodiment, vertical traction is additionally provided to a patient's leg by a support sling connected to a bar or some other overhead portion of a patient's bed such that the sling provides an uplifting force beneath a patient's lower leg. The resultant force of the horizontal and vertical traction provides the traction force necessary to bring and maintain the fracture fragments in close apposition and alignment.

In combination with the above, aligning and stabilizing members may be used to additionally position the fracture fragments of a patient's leg by releasably attaching to the solid polygon.

THE DRAWINGS

Other objects and advantages of the present invention will become apparent from the following detailed description of a preferred embodiment thereof taken in conjunction with the accompanying drawings, wherein:

FIG. 3 is a detailed axonometric view of the solid polygon of the subject invention and discloses the operable placement of securing and positioning members;

FIG. 4 is a detailed axonometric view of the various configurations of the aligning and stabilizing members in accordance with a preferred embodiment of the subject invention.

DETAILED DESCRIPTION

Figure 1:
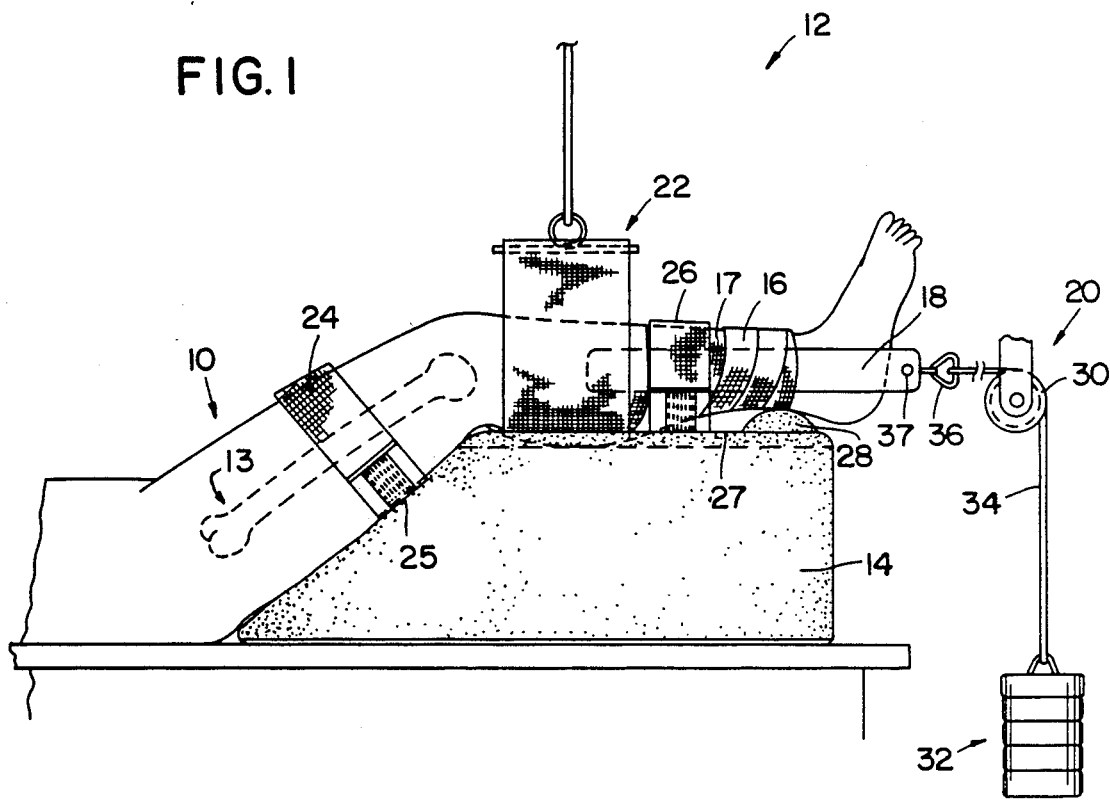
FIG. 1 is a side elevational view of a balanced skeletal traction apparatus and depicts the leg of a patient reclined in a recuperative supine position with traction force supplied to a fractured femur in accordance with a preferred embodiment of the invention.

Referring now to the drawings, wherein like numerals indicate like parts, and initially to FIG. 1, there will be seen an operative context of the subject invention. More particularly, the recuperating leg 10 of a patient lying in a supine recuperative position is shown positioned in a balanced skeletal traction apparatus 12 in accordance with a preferred embodiment of the subject invention. The balanced skeletal traction apparatus 12 provides traction force to the fracture fragments of a patient's femur 13 so that the fragments are maintained in close apposition and alignment during recuperation.

A solid polygon 14 elevates and supports the recuperating leg 10 of a patient while horizontal traction is provided by a lower leg sleeve member 16, a generally U-shaped support member 18, and tension assembly 20. Vertical traction is provided to the femur 13 by a support sling 22 which envelops the lower portion of a patient's recuperating leg 10. The support sling 22 is attached to a standard overhead apparatus available on most hospital beds or to a similarly functioning structure. A first securing strap 24 releasably secures a patient's upper leg to an inclined end surface 25 and a second securing strap 26 releasably secures a patient's lower leg to a generally horizontal upper surface 27 of the solid polygon 14. An aligning and stabilizing member 28 releasably attaches to the solid polygon 14 at any position along the inclined end surface 25 or the horizontal upper surface 27 to support various portions of a patient's recuperating leg 10 as needed.

The lower leg sleeve member 16 is composed of an elastomeric foam composition and has a longitudinal axis operable to lie along a patient's lower leg. The lower leg sleeve member 16 is flexible and elastically wraps around a patient's lower leg to securely embrace the lower leg.

The composition of the lower leg sleeve member 16 may be composed of a variety of materials but preferably is composed of a natural or synthetic foam rubber composition, polyurethane foam, or the like, which exhibits an elastic or resilient property and thus is operable to circumferentially grip a patient's lower leg in a manner to distribute normal forces all along the lower leg and provide an extended area of frictional engagement with the patient's lower leg.

In order to enhance binding contact, an elastic wrap 17 may be operably wound around the lower leg sleeve wrap 16 and the generally U-shaped support member 18 to secure the lower leg sleeve wrap 16 about a patient's lower leg. Further, this elastic wrap 17 has the synergistic advantage of supplementing and enhancing an even distribution of compressive forces along the patient's lower leg. In this embodiment, the U-shaped support member 18 is retained between the lower leg sleeve member 16 and the elastic strap 17 to provide rigidity to the lower leg sleeve member 16.

The tension assembly 20 comprises a pulley 30 and an associated stack of weights 32 attached to a traction cord 34. A connecting combination 36 integral with a first end of the U-shaped support member 18 connects the traction cord 34 to the U-shaped support member 18 so that a horizontal traction force may be provided to a patient's leg. The pulley 30 translates the direction of the vertical force of the weight 32 into a horizontal traction force. The horizontal traction force is variable and is a function of the mass of the stack of weights 32.

Figure 2:
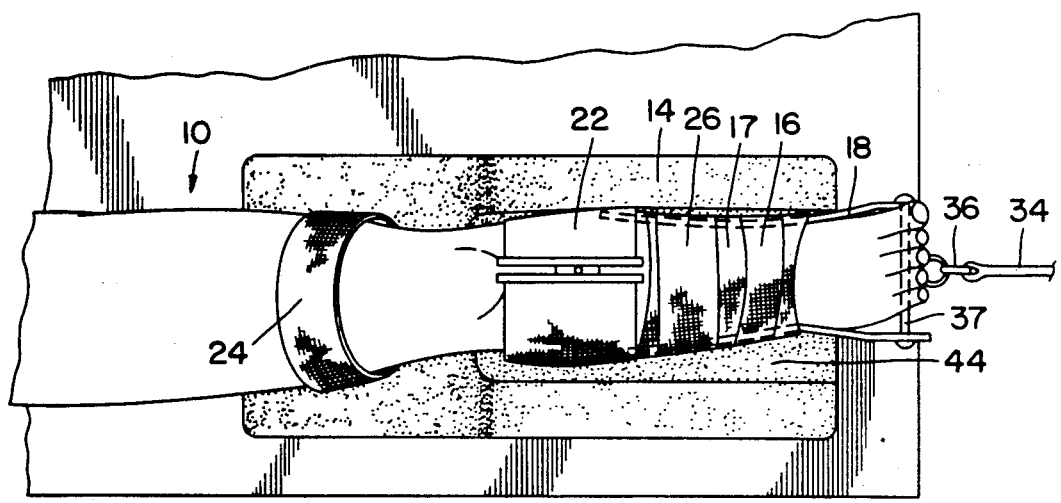
FIG. 2 is a plan view disclosing the operative context of the subject invention wherein a patient's leg is supplied with traction force necessary to maintain the fractured fragments in close apposition and alignment until successful healing occurs.

Referring to FIG. 2, a plan view of the subject balanced skeletal traction apparatus illustrates in more detail the configuration of the support member 18. Opposing lateral arms of the support member 18 define the shape of the lower leg sleeve member 16. The support member 18 is retained within and provides rigidity to the lower leg sleeve member 16 and connects to the tension assembly 20 at the distal end of the support member 18. The outer surface of the support arms of the support member 18 are connected to the inner surface of the lower leg sleeve member 16. A transverse bar 37 forming a byte portion connects the ends of the support arms of the support member 18. The support member 18 is preferably composed of a flexible aluminum alloy. The connecting combination 36 is attached to the transverse bar 37, as shown in FIG. 2.

Referring particularly to FIG. 3, there will be seen a detailed axonometric view of the solid polygon 14. The solid polygon 14 includes the inclined end surface 25, the generally horizontal upper surface 27, two generally vertical lateral sides 38 (one is not shown), a generally vertical distal end 40, and a substantially flat bottom surface 42. An elongated arcuate depression 44 in the surface of the horizontal upper surface 27 of the solid polygon 14 cradles and secures the lower portion of a patient's recuperating leg 10.

All surfaces of the solid polygon 14 except the flat bottom surface 42 are covered with a pile member of a hook and pile connecting combination, such as that sold under the trademark Velcro. The bottom surface 42 has a low coefficient of friction relative to the other surfaces of the solid polygon 14 which allows the solid polygon 14 to facilely slide across a bed surface when a patient desires minor readjustments in the position of the solid polygon 14.

The securing straps 24 and 26 are fashioned alike and both releasably attach to the solid polygon 14. The securing straps 24 and 26 an inner surface 45, which operably contacts a patient's leg, and an outer surface 46, and are made of elastic or a similar material which stretches as needed. More specifically, a first hook portion 47 of the outer surface 46 comprises a hook material of a hook and pile type connecting combination, such as the type commercially known as Velcro. A pile portion 48 of the inner surface 45 comprises pile material of a Velcro combination. The first hook portion 47 and pile portion 48 operably connect and permit the securing straps 24 and 26 to releasably embrace the patient's leg. A second hook portion 49 of the outer surface 46 operably engages with the solid polygon 14 as shown. A padded portion (not shown) of the inner surface 45 may also be provided to cushion the patient's leg when it is in contact with the inner surface 45.

The aligning and stabilizing member 28 may be transversely and releasably positioned anywhere along the inclined end surface 25 or the upper horizontal surface 27 of the solid polygon 14 to support and align portions of a patient's leg 10 as dictated by the particular location of a fracture. The aligning and stabilizing member 28 is a longitudinal segment of a solid cylinder composed of elastomeric foam. Shown in FIG. 3 is an aligning and stabilizing member 28 which comprises a one-half longitudinal section of a solid cylinder. The flat side 50 of the aligning and stabilizing member 28 is fashioned with a hook material of a Velcro combination which operably connects to the pile material of the solid polygon 14. FIG. 3 also illustrates the elastic nature of the aligning and stabilizing member 28 resulting from its elastomeric foam composition. This feature allows a patient's leg 10 to comfortably rest on the aligning and stabilizing member 28 and provides a degree of cushioning to the patient's leg 10.

FIG. 4 discloses the various shapes of the aligning and stabilizing member 28 which may be utilized to fulfill a variety of functions. All portions of longitudinal segments of a solid cylinder are connected to the solid polygon 14 as shown in FIG. 3. FIG. 4(A) shows an aligning and stabilizing member 28 as described and shown in FIG. 3. FIG. 4(B) shows a one-quarter longitudinal segment of a solid cylinder 52. A first flat surface 54 is covered with a hook material of a hook and pile connecting combination. A second flat surface 56, perpendicular to first flat surface 54, is uncovered elastomeric foam which operably contacts the surface of the patient's leg 10. The arcuate surface 58 of the one-quarter longitudinal segment of a solid cylinder 52 is covered with a pile material of a hook and pile connecting combination. FIG. 4(C) shows the same one-quarter longitudinal segment of a solid cylinder 52 of elastomeric foam positioned after ninety degrees of radial rotation. The rotated position of the one-quarter longitudinal segment of a solid cylinder 52 allows effective support and alignment of a patient's leg 10 at different positions which may require differently configured aligning and stabilizing members 28.

SUMMARY OF MAJOR ADVANTAGES OF THE INVENTION

After reading and understanding the foregoing inventive balanced skeletal traction apparatus, in conjunction with the drawings, it will be appreciated that several distinct advantages of the subject invention are obtained. Without attempting to set forth all of the desirable features of the instant balanced skeletal traction apparatus, at least some of the major advantages include the novel application of vertical and horizontal traction to a patient's recuperating leg 10 without use of a complex system of pulleys. The balanced skeletal traction apparatus 12 permits the fracture fragments of a patient's leg 10 to be facilely brought into close apposition to each other so that normal position, length, and alignment of the bone can be restored.

Use of the support sling 22 for vertical traction and the lower leg sleeve member 16 and corresponding U-shaped support member 18 for horizontal traction allow the patient's leg 10 to be assembled in the balanced skeletal traction apparatus 12 by a minimal number of personnel. Minimization of the number of personnel necessary to prepare and position the patient is brought about by obviation of the number of pulleys in the system. The stack of weights 32 can be facilely altered to produce a corresponding change in the magnitude of the horizontal traction force as necessitated during the duration of a patient's recuperation.

Use of aligning and stabilizing member 28 allows facile alignment and readjustment of the support available to a patient's leg 10. The elastomeric foam composition of the solid polygon 14 and the aligning and stabilizing member 28 provides cushioning to the patient's leg 10 and maximizes comfort.

Securing straps 24 and 26 insure secure connection of a patient's leg 10 to the solid polygon 14. Maintenance of the patient's leg 10 in a stable position is necessary for timely healing and rejoining of the patient's fracture fragments. The releasable nature of the securing straps 24 and 26 allows facile adjustment of the patient's leg 10 as needed during the recuperative process.

The elastomeric foam composition of both the solid polygon 14 and the aligning and stabilizing member 28 allow them to be easily manufactured, easily personalized to various sized patients, and inexpensive and thus disposable. The elastomeric foam also comfortably cushions the patient's leg 10.

The solid polygon 14 elevates the upper portion of the patient's leg 10 and encourages blood flow from the lower extremities, which is necessary for successful healing of the fracture fragments. The relatively low coefficient of friction of the bottom of the solid polygon 14 allows facile repositioning of the solid polygon 14 by a patient.

In describing the invention, reference has been made to a preferred embodiment and illustrative advantages of the invention. Those skilled in the art, however, and familiar with the instant disclosure of the subject invention, may recognize additions, deletions, modifications, substitutions and other changes which will fall within the purview of the subject invention and claims.

What is claimed is:

1. A balanced skeletal traction apparatus used for aligning fractured leg bones of a patient lying in a supine recuperative position following surgery or injury comprising:
   an underlying support member comprising a solid polygon having,
      an inclined end surface operable to be positioned beneath and coincident with a thigh portion of a patient's leg,
      a generally horizontal upper surface continuous with said inclined end surface, operable to support a patient's lower leg,
      two generally vertical lateral surfaces,
      a generally vertical distal end surface, and
      a substantially flat bottom surface;
   horizontal traction means operable to be connected to a patient's lower leg for providing longitudinal traction to a patient's leg for maintaining a patient's fracture fragments in close apposition and alignment during recuperation, said horizontal traction means comprising,
      tension means,
      a lower leg sleeve member having,
         a longitudinal axis operable to lie along a patient's lower leg and flexibly yet securely embrace a patient'lower leg, and
         at least one releasable retaining means for securing said lower leg sleeve member about a patient's lower leg, and
      a generally U-shaped support member having,
         a pair of support arms operable to extend along opposing lateral portions of a patient's lower leg and releasably connect to said lower leg sleeve wrap, and
      means to connect said generally U-shaped support member to said tension means; and
   at least one securing member operable to releasably secure a patient's leg with respect to at least one of said inclined end or horizontal upper surfaces of said underlying solid polygon for maintaining a desired lateral position of a patient's leg with respect to said underlying support member during patient recuperation.

2. A balanced skeletal traction apparatus as defined in claim 1 wherein:
   said generally horizontal upper surface is fashioned with an elongated arcuate depression which provides a cradle for receiving, restraining, and supporting a patient's lower leg.

3. A balanced skeletal traction apparatus as defined in claim 1 and further comprising:
   a support sling operable to supply a vertical traction force substantially normal to a longitudinal force supplied by said lateral traction means, and positioned to envelop the underside of a lower leg of a patient such that the resultant force of said vertical support sling and said lateral traction means provides adequate traction force to the fracture fragments of a patient's leg.

4. A balanced skeletal traction apparatus as defined in claim 1 and further comprising:
   at least one aligning and stabilizing member releasably connected to said underlying solid polygon and positioned to align a patient's leg as necessitated by the particular location of a fracture.

5. A balanced skeletal traction apparatus as defined in claim 4 wherein said at least one aligning and stabilizing member comprises:
   a plurality of aligning and stabilizing members to align various portions of a patient's leg as necessitated by the particular location of a fracture.

6. A balanced skeletal traction apparatus as defined in claim 4 or claim 5 wherein each of said aligning and stabilizing members comprises:
   a longitudinal segment of a solid cylinder, said longitudinal segment having one of a hook and pile connecting assembly attached thereto for releasable engagement of said longitudinal segment with said underlying solid polygon.

7. A balanced skeletal traction apparatus as defined in claim 6 wherein:
   at least one of said aligning and stabilizing members comprises a one-half longitudinal section of a solid cylinder.

8. A balanced skeletal traction apparatus as defined in claim 6 wherein:
   at least on of said aligning and stabilizing members comprises one-quarter longitudinal section of a solid cylinder.

9. A balanced skeletal traction apparatus as defined in claim 1 wherein said at least one securing member comprises:
   a releasably attachable band having a first surface composed of a hook material of a hook and pile type fastening combination.

10. A balanced skeletal traction apparatus as defined in claim 10 wherein said at least one securing member comprises:
    at least two securing members, said at least two securing members including,
    a first releasably attachable band operable to circumferentially envelop a lower portion of a patient's leg and attach to said generally horizontal upper surface of said underlying solid polygon, and
    a second releasably attachable band operable to circumferentially envelop an upper portion of a patient'leg and attach to said inclined upper end surface of said underlying solid polygon.

11. A balanced skeletal traction apparatus as defined in claim 1 wherein said substantially flat bottom surface of said underlying solid polygon comprises:
    a surface having a coefficient of friction less than the coefficient of friction of the remaining surfaces of said solid polygon.

12. A balanced skeletal traction apparatus as defined in claim 4 wherein:
    said underlying support member and said aligning and stabilizing member are comprised of elastomeric foam.

13. A balanced skeletal traction apparatus as defined in claim 1 wherein:
    said generally U-shaped support member is composed of a flexible, aluminum alloy.

14. A balanced skeletal traction apparatus as defined in claim 1 wherein said tension means comprises:
    a pulley suspended such that the upper surface of the pulley is horizontally coplanar with said support member;
    a weight; and
    a cord operable to engage with said pulley including,
    a first end connected to said means to connect to said tension means, and
    a second end connected to said weight.

15. A balanced skeletal traction apparatus used for aligning fractured leg bone of a patient lying in a supine recuperative position following surgery or injury comprising:
    an underlying support member comprising a solid polygon having,
       an inclined end surface operable to be positioned beneath and coincident with a thigh portion of a patient's leg,
       a generally horizontal upper surface continuous with said inclined end surface, operable to support a patient's lower leg,
       two generally vertical lateral surfaces,
       a generally vertical distal end surface, and
       a substantially flat bottom surface;
    horizontal traction means operable to be connected to a patient's lower leg for providing longitudinal traction to a patient's leg for maintaining a patient's fracture fragments in close apposition and alignment during recuperation;
    at least one securing member operable to releasably secure a patient's leg with respect to at least one of said inclined end or horizontal upper surfaces of said underlying solid polygon for maintaining a desired lateral position of a patient's leg with respect to said underlying support member during patient recuperation;
    at least one aligning and stabilizing member releasably connected to said underlying solid polygon and positioned to align a patient's leg as necessitated by the particular location of a fracture;
    an elongated arcuate depression fashioned on said generally horizontal upper surface which provides a cradle for receiving, restraining, and supporting a patient's lower leg; and
    said at least one securing member comprises a releasably attachable band having a first surface composed of one of a hook and pile type fastening material and having,
       a first releasably attachable band operable to circumferentially envelop a lower portion of a patient's leg and attach to said generally horizontal upper surface of said underlying solid polygon, and
       a second releasably attachable band operable to circumferentially envelop an upper portion of a patient's leg and attach to said inclined upper end surface of said underlying solid polygon.

16. A balanced skeletal traction apparatus as defined in claim 15 and further comprising:
    a support sling operable to supply a vertical traction force substantially normal to a longitudinal force supplied by said lateral traction means, and positioned to envelop the underside of a lower leg of a patient such that the resultant force of said vertical support sling and said lateral traction means provides adequate traction force to the fracture fragments of a patient's leg.

17. A balanced skeletal traction apparatus as defined in claim 15 wherein:
at least one of said aligning and positioning members comprises a one-half longitudinal section of a solid cylinder having one of a hook and pile connecting assembly attached thereto for releasable engagement of said longitudinal segment with said underlying solid polygon.

18. A balanced skeletal traction apparatus as defined in claim 15 wherein:
at least one of said aligning and stabilizing members comprises a one-quarter longitudinal section of a solid cylinder having one of a hook and pile connecting assembly attached thereto for releasable engagement of said longitudinal segment with said underlying solid polygon.

19. A balanced skeletal traction apparatus as defined in claim 15 wherein said horizontal traction means comprises:
tension means;
a lower leg sleeve member having,
a longitudinal axis operable to lie along a patient's lower leg and flexibly yet securely embrace a patient's lower leg, and
at least one releasable retaining means for securing said lower leg sleeve member about a patient's lower leg; and
a generally U-shaped support member having,
a pair of support arms operable to extend along opposing lateral portions of a patient's lower leg and releasably connect to said lower leg sleeve member, and
means to connect said generally U-shaped support member to said tension means.

* * * * *